United States Patent
Trepanier et al.

(10) Patent No.: US 10,980,687 B2
(45) Date of Patent: Apr. 20, 2021

(54) TECHNIQUES FOR GENERATING AUDITORY AND HAPTIC OUTPUT WITH A VIBRATIONAL PANEL OF A PATIENT SUPPORT APPARATUS

(71) Applicant: Stryker Corporation, Kalamazoo, MI (US)

(72) Inventors: Jerald A. Trepanier, Augusta, MI (US); Scott A. Kuebler, Delton, MI (US); Krishna S. Bhimavarapu, Kalamazoo, MI (US); Marko N. Kostic, Johnson City, TN (US); Jonathan M. Greenbank, Plainwell, MI (US)

(73) Assignee: Stryker Corporation, Kalamazoo, MI (US)

(*) Notice: Subject to any disclaimer, the term of this patent is extended or adjusted under 35 U.S.C. 154(b) by 117 days.

(21) Appl. No.: 16/040,195

(22) Filed: Jul. 19, 2018

(65) Prior Publication Data
US 2019/0021924 A1 Jan. 24, 2019

Related U.S. Application Data

(60) Provisional application No. 62/534,480, filed on Jul. 19, 2017.

(51) Int. Cl.
*A61G 7/05* (2006.01)
*G06F 3/01* (2006.01)
(Continued)

(52) U.S. Cl.
CPC .............. *A61G 7/05* (2013.01); *A61B 5/746* (2013.01); *A61H 1/005* (2013.01); *G06F 3/016* (2013.01);
(Continued)

(58) Field of Classification Search
CPC ...... A61G 7/05; A61G 7/0506; A61G 7/0524; A61G 5/746; A61G 5/002; A61H 23/00;
(Continued)

(56) References Cited

U.S. PATENT DOCUMENTS 4,047,377 A 9/1977 Banks, Jr.
4,603,317 A 7/1986 Gailbreath et al.
(Continued)

FOREIGN PATENT DOCUMENTS

EP 2505175 A1 10/2012

OTHER PUBLICATIONS

Aito, "Haptic-Touch Technology Video", https://aito-touch.com/technology/haptic-touch/, Jul. 2017.
(Continued)

*Primary Examiner* — David R Hare
(74) *Attorney, Agent, or Firm* — Howard & Howard Attorneys PLLC

(57) ABSTRACT

A patient support apparatus comprises a base and a support structure coupled to the base and being configured to support a patient. The apparatus also comprises a panel having a surface and being physically adapted to vibrate at one or more frequencies, a controller configured to generate an electrical signal, and a vibrational exciter. The vibrational exciter comprises a surface coupled to the surface of the panel and being configured to receive the electrical signal from the controller and to convert the electrical signal into vibrational energy. The surface of the vibrational exciter is configured to transfer the vibrational energy to the surface of the panel to vibrate the panel at the one or more frequencies.

21 Claims, 10 Drawing Sheets

(51) Int. Cl.
*G16H 40/20* (2018.01)
*G06F 3/0346* (2013.01)
*A61H 1/00* (2006.01)
*A61B 5/00* (2006.01)
*G16H 40/63* (2018.01)

(52) U.S. Cl.
CPC ........... *G06F 3/0346* (2013.01); *G16H 40/20* (2018.01); *G16H 40/63* (2018.01); *A61B 5/002* (2013.01); *A61G 7/0506* (2013.01); *A61G 7/0524* (2016.11); *A61H 2201/0142* (2013.01); *A61H 2201/1207* (2013.01); *A61H 2201/5023* (2013.01); *A61H 2201/5025* (2013.01); *A61H 2201/5046* (2013.01); *A61H 2201/5058* (2013.01); *A61H 2201/5071* (2013.01); *A61H 2201/5084* (2013.01); *A61H 2201/5097* (2013.01); *A61H 2203/0443* (2013.01)

(58) Field of Classification Search
CPC ................ A61H 23/0236; A61H 1/005; A61H 2201/0142; A61H 2201/5025; A61H 2201/5046; A61H 2201/1207; A61H 2201/5023; A61H 2201/5071; A61H 2201/5097; A61H 2201/5084; A61H 2201/5058; A61H 2203/0443; G16H 40/63; G16H 40/20; G06F 3/0346; G06F 3/016
See application file for complete search history.

(56) References Cited

U.S. PATENT DOCUMENTS

| | | | |
|---|---|---|---|
| 5,007,410 A | 4/1991 | DeLaney | |
| 5,590,241 A | 12/1996 | Park et al. | |
| 5,828,314 A | 10/1998 | Park | |
| 7,148,875 B2* | 12/2006 | Rosenberg | G06F 3/03547 345/156 |
| 8,018,328 B2 | 9/2011 | Goldstein et al. | |
| 8,038,632 B2 | 10/2011 | Flick et al. | |
| 8,141,947 B2* | 3/2012 | Nathan | B60N 2/976 297/217.3 |
| 8,484,777 B2 | 7/2013 | Shih | |
| 8,896,524 B2* | 11/2014 | Birnbaum | G06F 3/016 345/156 |
| 8,976,975 B2 | 3/2015 | Loud | |
| 9,380,982 B2 | 7/2016 | Battista, Jr. | |
| 9,414,964 B2 | 8/2016 | Censo et al. | |
| 9,503,803 B2 | 11/2016 | Gauger, Jr. et al. | |
| 9,851,805 B2* | 12/2017 | Levesque | A63F 13/285 |
| 10,449,101 B2* | 10/2019 | Brosnan | A61G 7/0524 |
| 2004/0021351 A1 | 2/2004 | House | |
| 2007/0050910 A1* | 3/2007 | Blanchard | A61H 9/0078 5/617 |
| 2008/0303797 A1 | 12/2008 | Grothe | |
| 2009/0100599 A1 | 4/2009 | Rawls-Meehan | |
| 2011/0030141 A1* | 2/2011 | Soderberg | A61G 7/015 5/600 |
| 2011/0199342 A1* | 8/2011 | Vartanian | G06F 3/04845 345/177 |
| 2011/0260995 A1* | 10/2011 | Woo | G06F 3/016 345/173 |
| 2012/0194483 A1 | 8/2012 | Deluca | |
| 2013/0063258 A1 | 3/2013 | Mitsugi et al. | |
| 2014/0379369 A1* | 12/2014 | Kokovidis | A61B 5/002 705/2 |
| 2015/0077534 A1 | 3/2015 | Derenne et al. | |
| 2016/0005308 A1 | 1/2016 | Kohlrausch et al. | |
| 2016/0195931 A1* | 7/2016 | Czelnik | G06F 3/016 345/173 |
| 2016/0349854 A1* | 12/2016 | Hayes | G06F 1/3262 |
| 2016/0354263 A1 | 12/2016 | Furman et al. | |
| 2017/0143565 A1* | 5/2017 | Childs | A61G 7/018 |
| 2017/0173262 A1* | 6/2017 | Veltz | A61B 5/0022 |
| 2017/0357317 A1* | 12/2017 | Chaudhri | H04M 1/72552 |
| 2018/0110445 A1 | 4/2018 | Bhimavarapu et al. | |
| 2018/0151035 A1* | 5/2018 | Maalouf | G06F 3/017 |
| 2018/0153752 A1* | 6/2018 | Kostic | A61G 7/0509 |

OTHER PUBLICATIONS

Aito, "Haptic-Touch Webpage", www.aito-touch.com/technology, Jul. 2017, 7 pages.
Apple, "How to Use the Home Button on Iphone 7 and Iphone 8", www.support.apple.com/en-us/HT207188,2017, 2 pages.
Pui Audio, Inc., "The Invisible Speaker"—PUI audio eXciters White Paper, 2017, 6 pages.

* cited by examiner

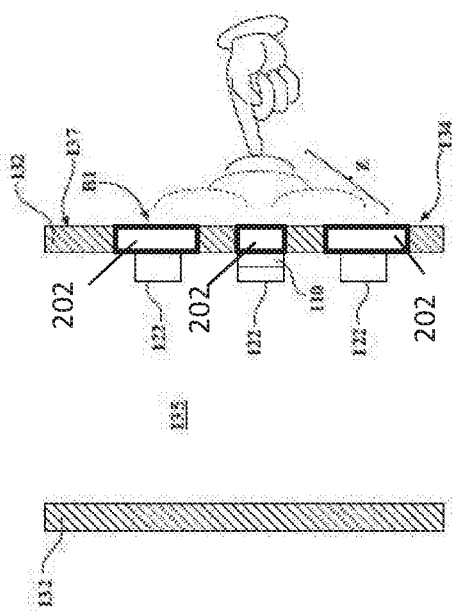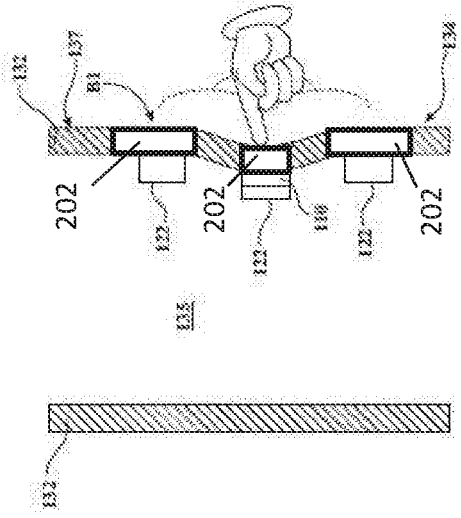

US 10,980,687 B2

TECHNIQUES FOR GENERATING AUDITORY AND HAPTIC OUTPUT WITH A VIBRATIONAL PANEL OF A PATIENT SUPPORT APPARATUS

RELATED APPLICATIONS

This application claims the benefit of and priority to U.S. provisional patent application no. 62/534,480, filed on Jul. 19, 2017, the entire contents and disclosure of which are hereby incorporated by reference.

BACKGROUND

Patient support apparatuses, such as hospital beds, stretchers, cots, tables, wheelchairs, and chairs facilitate care of patients in a health care setting. Conventional patient support apparatuses comprise a base and a patient support surface upon which the patient is supported. Often, these patient support apparatuses have one or more powered devices to perform one or more functions on the patient support apparatus. These functions can include lifting or lowering the patient support surface, extending or shortening a length of the patient support apparatus, extending or narrowing a width of the patient support apparatus, raising or lowering one or more deck sections, and the like. When a caregiver wishes to perform such a function, the caregiver actuates a user input device on a user interface, often in the form of a button on a control panel. Conventional user interfaces include separate modules (e.g., touchscreen displays) attached to one or more side rails, a headboard, and/or a footboard of the patient support apparatus and are generally difficult to clean due to the nature of the materials employed and seams/joints that are formed around the user interface. This can be particularly problematic as caregivers, patients, and other users are constantly touching the user interface to control the functions of the patient support apparatus. As a result, the user interface is especially susceptible to contamination by bacteria, viruses, and other microorganisms, which can lead to the spread of infections.

Similar problems may occur with delivering sound to patients or caregivers. Patient support apparatuses often include speakers for delivering audible notifications to patients or caregivers when operating a user interface or when interfacing with a caregiver callback station, for example. Speakers may also be used to play music or videos at the patient support apparatus. Conventional speakers include a diaphragm that is disposed behind a grill or mesh to protect the diaphragm from damage. The grill or mesh can collect and trap dust, dirt, biomaterials, or other mediums that support bacteria, viruses, and other microorganisms.

A patient support apparatus designed to address one or more of the aforementioned challenges is desired.

BRIEF DESCRIPTION OF THE DRAWINGS

FIG. 8A is a cross-sectional view taken along the line 8-8 in FIG. 7 illustrating a vibration generation system to provide haptic sensations.
FIG. 8B is a cross-sectional view taken along the line 8-8 in FIG. 7 illustrating actuation of a sensor.

DETAILED DESCRIPTION

Figure 1:
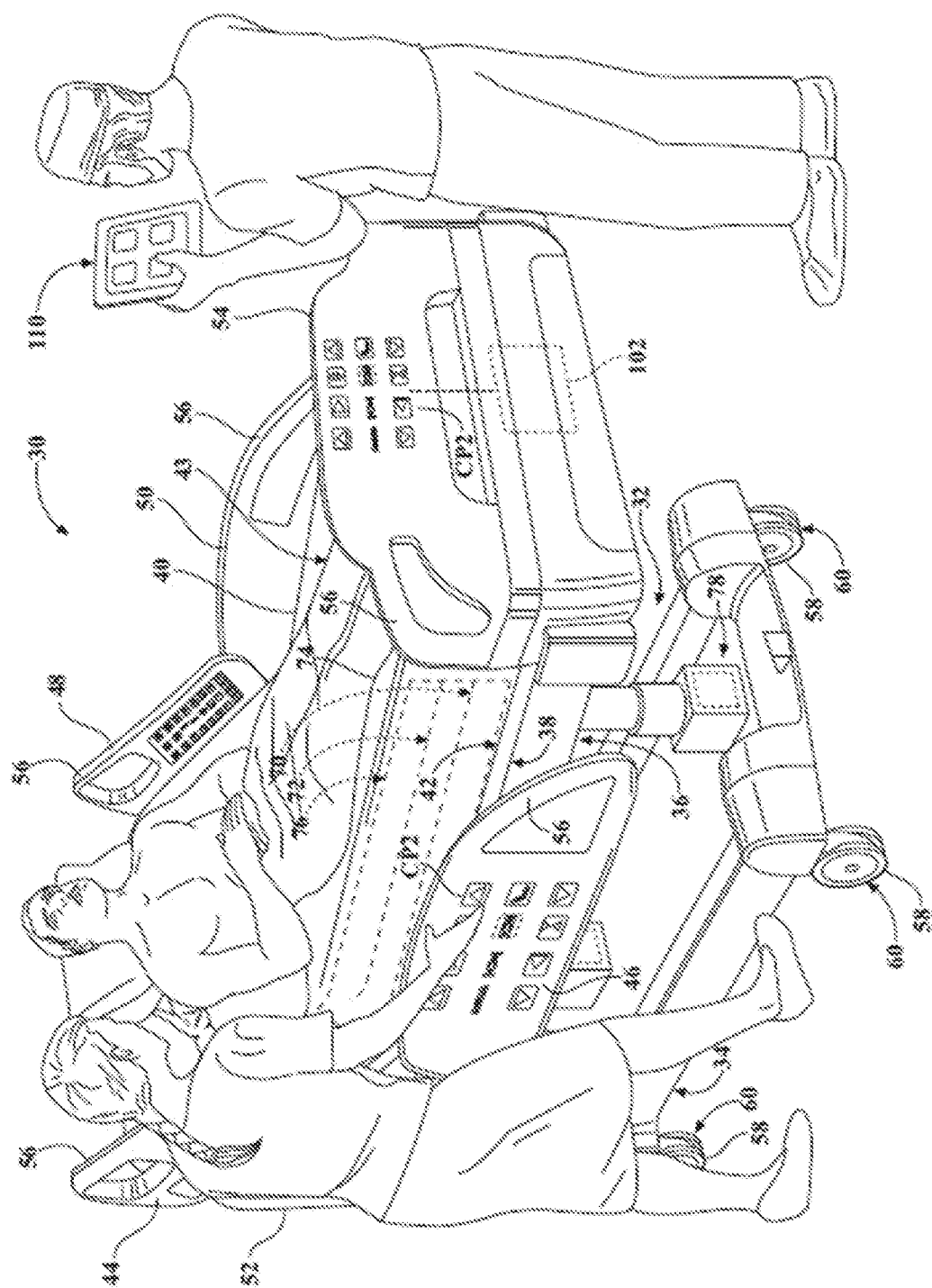
FIG. 1 is perspective view of a patient support apparatus.

Referring to FIG. 1, a patient support system comprising a patient support apparatus 30 is shown for supporting a patient in a health care setting. The patient support apparatus 30 illustrated in FIG. 1 comprises a hospital bed. In other embodiments, however, the patient support apparatus 30 may comprise a stretcher, cot, table, wheelchair, chair, or similar apparatus utilized in the care of a patient.

A support structure 32 provides support for the patient. The support structure 32 illustrated in FIG. 1 comprises a base 34 and an intermediate frame 36. The intermediate frame 36 is spaced above the base 34. The support structure 32 also comprises a patient support deck 38 disposed on the intermediate frame 36. The patient support deck 38 comprises several sections, some of which are capable of articulating (e.g., pivoting) relative to the intermediate frame 36, such as a fowler section, a seat section, a thigh section, and a foot section. The patient support deck 38 provides a patient support surface 42 upon which the patient is supported.

A mattress 40 is disposed on the patient support deck 38. The mattress 40 comprises a secondary patient support surface 43 upon which the patient is supported. The base 34, intermediate frame 36, patient support deck 38, and patient support surfaces 42, 43 each have a head end and a foot end corresponding to designated placement of the patient's head and feet on the patient support apparatus 30. The construction of the support structure 32 may take on any known or conventional design, and is not limited to that specifically set forth above. In addition, the mattress 40 may be omitted in certain embodiments, such that the patient rests directly on the patient support surface 42.

Side rails 44, 46, 48, 50 are coupled to the intermediate frame 36 and are thereby supported by the base 34. A first side rail 44 is positioned at a right head end of the intermediate frame 36. A second side rail 46 is positioned at a right foot end of the intermediate frame 36. A third side rail 48 is positioned at a left head end of the intermediate frame 36. A fourth side rail 50 is positioned at a left foot end of the intermediate frame 36. If the patient support apparatus 30 is a stretcher or a cot, there may be fewer side rails. The side rails 44, 46, 48, 50 are movable between a raised position in which they block ingress and egress into and out of the patient support apparatus 30, one or more intermediate positions, and a lowered position in which they are not an obstacle to such ingress and egress. In still other configurations, the patient support apparatus 30 may not include any side rails.

A headboard 52 and a footboard 54 are coupled to the intermediate frame 36. In other embodiments, when the headboard 52 and footboard 54 are included, the headboard 52 and footboard 54 may be coupled to other locations on the patient support apparatus 30, such as the base 34. In still other embodiments, the patient support apparatus 30 does not include the headboard 52 and/or the footboard 54.

Caregiver interfaces 56, such as handles, are shown integrated into the footboard 54 and side rails 44, 46, 48, 50 to facilitate movement of the patient support apparatus 30 over floor surfaces. Additional caregiver interfaces 56 may be integrated into the headboard 52 and/or other components of the patient support apparatus 30. The caregiver interfaces 56 are graspable by the caregiver to manipulate the patient support apparatus 30 for movement.

Other forms of the caregiver interface 56 are also contemplated. The caregiver interface 56 may comprise one or more handles coupled to the intermediate frame 36. The caregiver interface 56 may simply be a surface on the patient support apparatus 30 upon which the caregiver applies force to cause movement of the patient support apparatus 30 in one or more directions, also referred to as a push location. This may comprise one or more surfaces on the intermediate frame 36 or base 34. This could also comprise one or more surfaces on or adjacent to the headboard 52, footboard 54, and/or side rails 44, 46, 48, 50. In other embodiments, the caregiver interface 56 may comprise separate handles for each hand of the caregiver. For example, the caregiver interface 56 may comprise two handles.

Wheels 58 are coupled to the base 34 to facilitate transport over the floor surfaces. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. It should be understood that various configurations of the caster assemblies 60 are contemplated. In addition, in some embodiments, the wheels 58 are not caster wheels and may be non-steerable, steerable, non-powered, powered, or combinations thereof. Additional wheels are also contemplated. For example, the patient support apparatus 30 may comprise four non-powered, non-steerable wheels, along with one or more powered wheels. In some cases, the patient support apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 60 and contact the floor surface in the deployed position, they cause two of the caster assemblies 60 to be lifted off the floor surface thereby shortening a wheel base of the patient support apparatus 30. A fifth wheel may also be arranged substantially in a center of the base 34.

Figure 2:
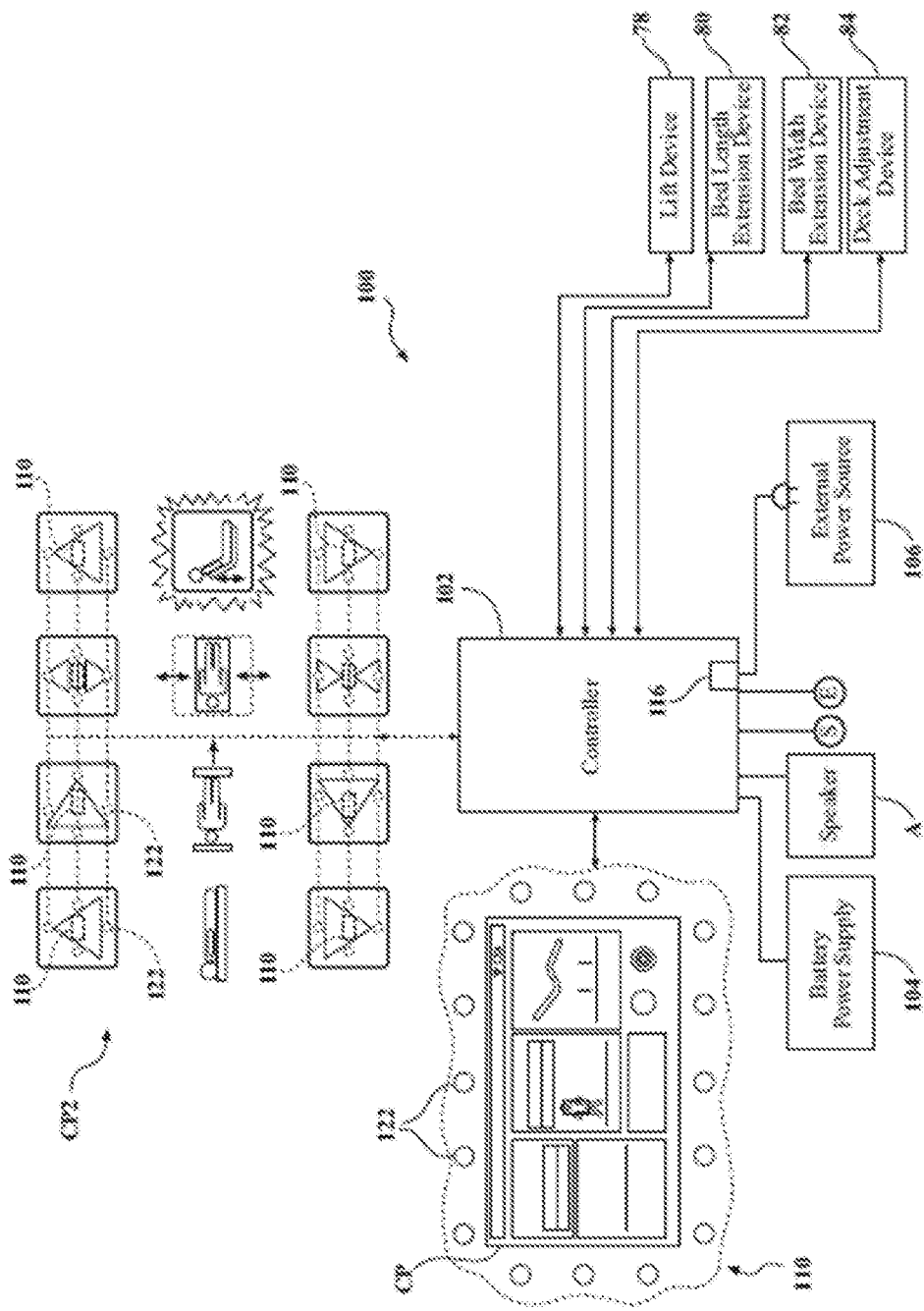
FIG. 2 is a schematic view of a control system.

Referring to FIG. 2, the patient support system may comprise one or more powered devices 78-84, each configured to perform one or more predetermined functions. The powered devices 78-84 utilize one or more components that require electricity. The powered devices 78-84 may comprise powered adjustment devices 78-84, such as a lift device 78, a bed length extension device 80, a bed width extension device 82, and a deck adjustment device 84. Other powered devices, such as powered wheels, and the like, are also contemplated. For instance, percussion devices, compression devices, vibration devices, and other patient therapy devices may also be employed.

A control system 100 is provided to control operation of the powered devices 78-84. The control system 100 comprises a controller 102 having one or more microprocessors for processing instructions or for processing an algorithm stored in memory 116 to control operation of the powered devices 78-84. Additionally or alternatively, the controller 102 may comprise one or more microcontrollers, field programmable gate arrays, systems on a chip, discrete circuitry, and/or other suitable hardware, software, or firmware that is capable of carrying out the functions described herein. The controller 102 may be carried on-board the patient support apparatus 30, or may be remotely located. In one embodiment, the controller 102 is mounted to the base 34. In other embodiments, the controller 102 is mounted to the footboard 54. The controller 102 may comprise one or more subcontrollers configured to control all the powered devices 78-84 or one or more subcontrollers for each of the powered devices 78-84. Power to the powered devices 78-84 and/or the controller 102 may be provided by a battery power supply 104 and/or an external power source 106.

The controller 102 is coupled to the powered devices 78-84 in a manner that allows the controller 102 to control the powered devices 78-84. The controller 102 may communicate with the powered devices 78-84 via wired or wireless connections. The controller 102 generates and transmits control signals to the powered devices 78-84, or components thereof, to operate their associated actuators, control their pumps, control their valves, or otherwise cause the powered devices 78-84 to perform one of more of the desired functions.

The controller 102 monitors a current state of the powered devices 78-84 and determines desired states in which the powered devices 78-84 should be placed, based on one or more input signals that the controller 102 receives from one or more user input devices 110. The state of the powered device 78-84 may be a position, a relative position, a pressure, an intensity, a frequency, an amplitude, a period, an angle, a speed, an energization status (e.g., on/off), or any other parameter of the powered device 78-84.

The user input devices 110 may comprise, for instance, piezoelectric sensors that measure deflection or pressure when contacted by the user. The user input devices 110 may also comprise one or more buttons that are directly contacted by the user and that physically move when pressure is applied by the user. Other types of sensors may comprise pressure sensors, strain gauges, temperature sensors, optical sensors, and the like. Other types of sensors are also contemplated.

The caregiver, or other user, may actuate one of the user input devices 110, which transmits a corresponding input signal to the controller 102, and the controller 102 controls operation of the powered device 78-84 based on the input signal. Operation of the powered device 78-84 may continue until the caregiver discontinues actuation of the user input device 110, e.g., until the input signal is terminated. In other words, depending on which user input device 110 is engaged, i.e., what input signal is received by the controller 102, the controller 102 controls operation of one of the powered devices 78-84. In certain embodiments, the controller 102 selects or initiates operation of one of the powered devices 78-84 based on the input signals received by the controller 102. The user input devices 110 may be located on one of the side rails 44, 46, 48, 50, the headboard 52, the footboard 54, or other suitable locations. The user input devices 110 may also be located on a portable electronic device (e.g., iWatch®, iPhone®, iPad®, or similar electronic devices), as shown in FIG. 1.

Figure 3:
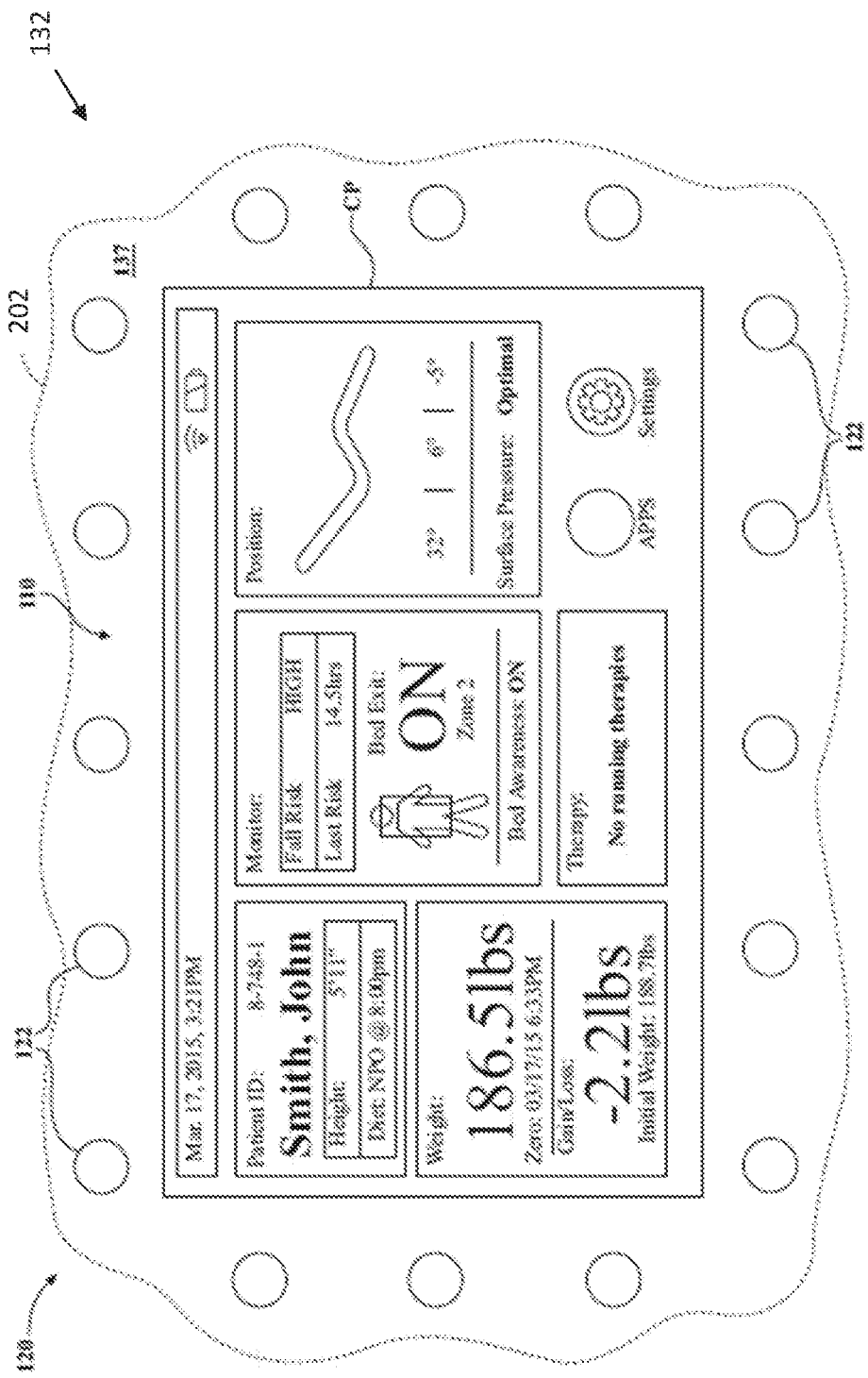
FIG. 3 is an illustration of a control panel.

In one embodiment shown in FIGS. 2 and 3, the patient support apparatus 30 comprises a control panel CP having a user input device 110 in the form of a touchscreen to enable a user to control one or more functions of the patient support apparatus 30. The control panel CP may be integrated into one or more of the side rails 44, 46, 48, 50, headboard 52, footboard 54, or any other components of the patient support apparatus 30. Alternatively, the control panel CP may be integrated within a pendant or other device wearable by the user. The touchscreen of the control panel CP displays a graphical user interface (GUI) to facilitate control of the powered devices 78-84. The control panel CP may also comprise a display to display certain information as shown. As should be appreciated, the patient support apparatus 30 may comprise any number of powered devices 78-84 and corresponding user input devices 110.

As shown in FIG. 3, a vibration generation system 120 cooperates with the control panel CP to provide haptic sensations (e.g., tactile stimuli) and/or auditory outputs to a user of the control panel CP. In one example, the vibration generation system 120 comprises an array of vibrational exciters 122. In the embodiment shown, the vibrational exciters 122 are arranged about a periphery of the control panel CP and are embedded in a panel 202 (described more fully with respect to FIG. 9). In one embodiment, the panel 202 may be incorporated within a barrier wall 132 of the patient support apparatus 30. The barrier wall 132 may be a wall of one of the side rails 44, 46, 48, 50, headboard 52, footboard 54, or other component of the patient support apparatus 30. In one embodiment, the barrier wall 132 may be formed of an electrically non-conductive material, such as plastic, wood, certain composites, and the like. In other embodiments, the barrier wall 132 may be formed of an electrically conductive material, such as sheet metal (e.g., aluminum, steel, etc.), or another suitable material.

The barrier wall 132 is formed of a material that can be easily sanitized to control the spread of infection. The barrier wall 132 may include an exterior surface 137 that faces the patient or caregiver. Accordingly, the panel 202 may be a portion of the barrier wall 132 (e.g., a portion of the exterior surface 137) or may replace a portion of the barrier wall 132. In another embodiment, the panel 202 may include the entire exterior surface 137 of the barrier wall 132. The panel may be more rigid than the barrier wall 132 or may be more flexible than the barrier wall 132 as described more fully herein. In other embodiments, the vibrational exciters 122 may be integrated into a panel 202 that includes the control panel CP or elsewise located with respect to the control panel CP. The vibrational exciters 122 may be hidden behind the panel 202.

The vibration generation system 120 may be arranged and controlled by the controller 102 to provide haptic sensations and/or auditory outputs to the user. The auditory outputs may be associated with selectable items (e.g., icons) on the touchscreen so that the user receives auditory confirmation when the selectable items are operated by the user. The user may operate the selectable items by contacting or positioning the user's finger in close proximity to the selectable items. The vibrational exciter 122 converts electrical signals received from the controller 102 to vibrational energy that is then transmitted to the user as auditory and/or haptically sensed pressure waves as described more fully herein.

The auditory outputs may also be associated with audio files or other audio signals transmitted by the controller 102. For example, the user may select one or more music or video files to play through an entertainment system operated through patient support apparatus 30. The controller 102 may transmit the audio portion of the selected entertainment option as one or more audio signals to the vibrational exciter 122. The vibrational exciter 122 may then convert the audio signals to vibrations, which are propagated using panels 202 or other portions of patient support apparatus 30 as auditory pressure waves. The auditory pressure waves propagate through the ambient air to reach the user, causing the user to perceive the sounds associated therewith. In a similar manner, other audio may be transmitted to the user using the vibrational exciters 122, such as spoken audio from a caregiver at a caregiver callback station or through a caregiver's mobile computing device, for example.

The haptic sensations may be associated with selectable items on the touchscreen so that the user feels a tactile sensation as the user's finger approaches and/or contacts the selectable items. The haptic sensations can be generated in a manner that provides a virtual button to the user so that, even though the touchscreen is flat and devoid of tactilely significant surfaces, the user is given the impression that a raised button actually exists. Such a virtual button can be created by pressure waves directed toward the user's finger that are felt by the user as the user's finger approaches and/or contacts the touchscreen, thereby creating tactile stimuli on the user's finger (see the graphical representation of ultrasound waves in FIG. 4). The haptic sensations can also be generated in a manner that conveys information to the user (also referred to as informational haptic feedback), such as patient conditions or alarm conditions. For example, when the user has reached maximum or minimum limits of one or more of the powered devices, the pressure waves may pulse, increase in intensity, decrease in intensity, etc. The controller 102 may provide the haptic sensations through texturizing. Texturizing involves providing controlled pressure waves via the vibration generation system 120 to provide or simulate friction sensations, pulsing sensations, variable thickness sensations, coarseness sensations, irregularity sensations, movement sensations, bumpiness sensations, rigidness sensations, pliability sensations, and the like. The texturizing of user interface elements and other forms of haptic feedback provided by the vibrational exciters 122 may be similar to those described in U.S. Patent Application Publication No. 2018/0153752, entitled "Haptic Systems and Methods for a User Interface of a Patient Support Apparatus", the disclosure of which is hereby incorporated by reference in its entirety.

In some embodiments, pressure waves reach the user, and provide haptic sensations to the user, before the user reaches any actual surface of the control panel CP. Accordingly, this can be referred to as contactless, haptic sensations. In some cases, such as when the haptic sensations are combined with user interfaces that have touchless/contactless input devices (e.g., gesture-based input, optical input, etc.), the combination of contactless haptic sensations and contactless user input reduces infections that may otherwise spread due to contact with the user interface. See, for example, U.S. Patent Application Publication No. 2015/0077534, entitled "Person Support Apparatuses With Virtual Control Panels," which is hereby incorporated by reference. See also, U.S. Patent Application Publication No 2011/0199342, which is hereby incorporated by reference. When virtual control panels like those disclosed in these publications are employed along with the contactless haptic systems and methods described herein, direct infectious transmission between the user and the patient support apparatus 30 can be reduced.

Figure 4:
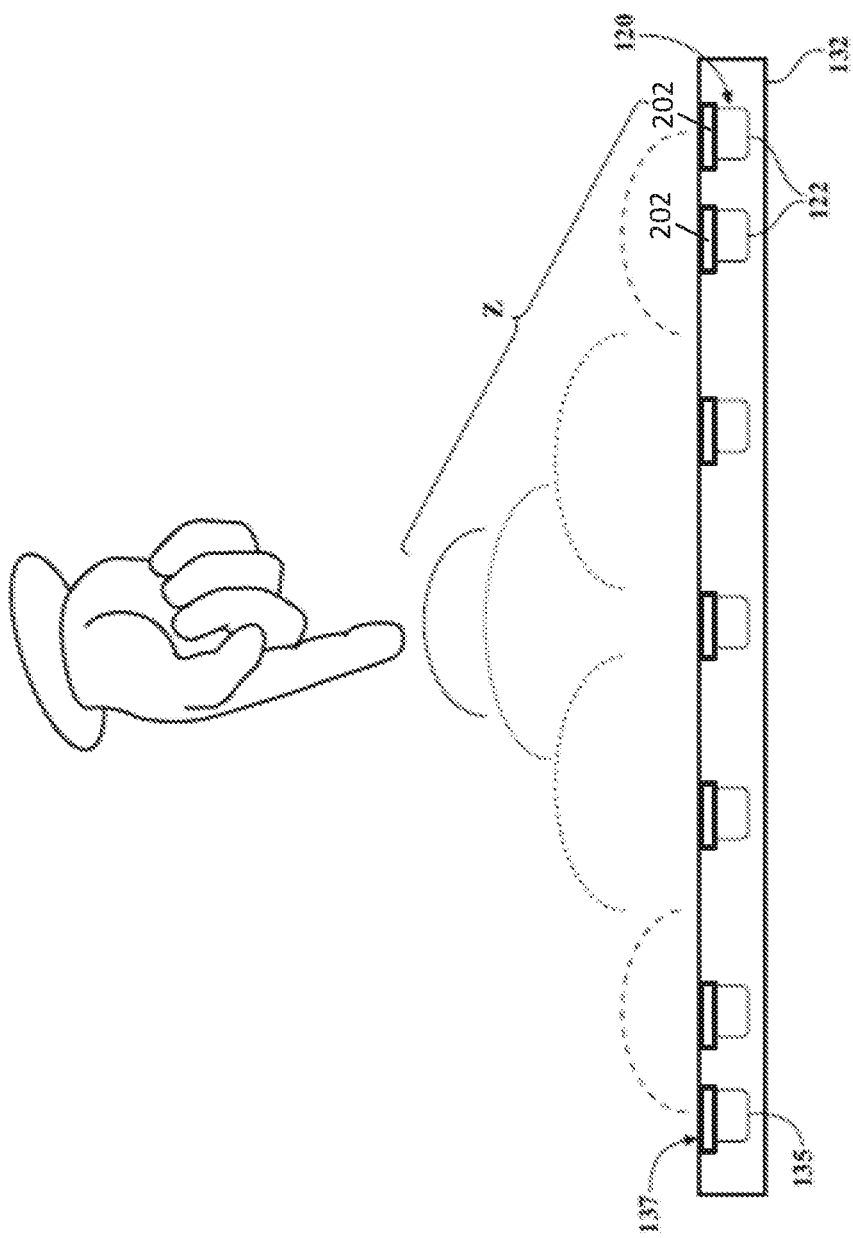
FIG. 4 is an illustration of a haptic sensation zone.

Referring to FIG. 4, the vibrational exciters 122 may emit directional pressure waves through a medium (such as air) to desired locations beyond the panel 202 in a sensation zone Z. The sensation zone Z is defined as a space, part of the space, or a force field beyond the panel 202 that defines the range of haptic perception. Pressure waves may also be emitted from the vibrational exciters 122 in various patterns to create different sensations.

The controller 102 is configured to control the intensity (e.g., strength or amplitude) or frequency of pressure wave emission. Pressure wave intensity and/or frequency may be varied over time to provide different sensations to the user (e.g., the user's finger, hand, etc.). In one embodiment, as the user's finger pulls away from the panel 202 or the control panel CP embodied therein, intensity may be reduced by the controller 102. When the user's finger moves toward the panel 202 or the control panel CP, the intensity may be increased. The example of FIG. 4 shows a spaced relationship between the user's hand and the panel 202 or control panel CP when generating pressure waves with the vibrational exciters 122. However, it should be reiterated that the vibrational exciters 122 may emit directional pressure waves directly to the user's hand through the panel 202 or control panel CP without passing through air as the user directly contacts the panel 202 or control panel CP.

Figure 6:
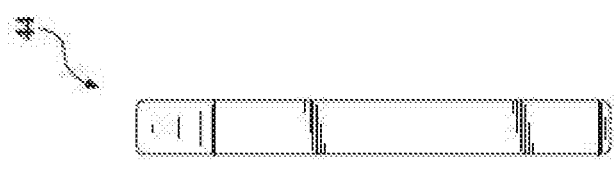
FIG. 6 is a right side elevational view of the side rail from FIG. 5.
Figure 5:
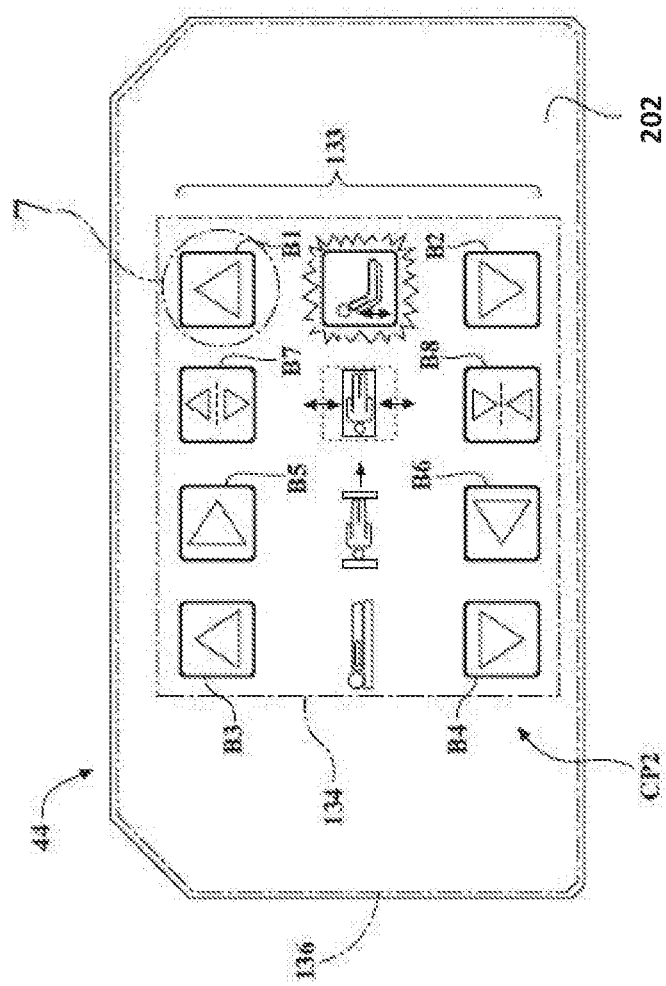
FIG. 5 is a front elevational view of a second control panel integrated into a sanitizable barrier wall of a side rail.

Referring to FIG. 5, in another embodiment, another control panel CP2 is shown integrated into the panel 202. The control panel CP2 may be integrated into a panel 202 within one of the side rails 44, 46, 48, 50, headboard 52, footboard 54, or any other component of the patient support apparatus 30. In FIG. 5, the control panel CP2 is shown integrated into a panel 202 formed within the side rail 44. An end view of the side rail 44 is shown in FIG. 6. In an alternative embodiment, the functionality of the control panel CP2 may be integrated into the control panel CP.

The control panel CP2 comprises non-electronic indicia 133 disposed on the panel 202. The indicia 133 is visible to the user and is located in a first region 134. The indicia 133 is shown fixed to an exterior surface of the panel 202. In one example, the indicia 133 comprises printed material on the exterior surface of the panel 202. In another embodiment, the indicia 133 is provided on a separate indicia layer (not shown) attached to the panel 202. The indicia layer may comprise an adhesive backing to adhere to the panel 202. The panel 202 also comprises a second region 136 free of indicia adjacent the first region 134. In this embodiment, the exterior surface of the panel 202 is continuous between the first region 134 and the second region 136. The exterior surface of the panel 202 is also free of seams between the first region 134 and the second region 136. Furthermore, in the embodiments that lack joints/seams in the panel 202 between the first region 134 and the second region 136, the exterior surface of the panel 202 can be easily wiped down with sanitizing wipes, etc. to inhibit the spread of infection.

The indicia 133 may comprise separate indicia B1-B8 associated with different predetermined functions of one or more of the powered devices 78-84. As users are generally accustomed to physical buttons that have symbols or other forms of indicia, the separate indicia B1-B8 may be similar in form to those conventionally used on push-button user interfaces. In this case, however, the vibration generation system 120 (not shown in FIG. 5) provides haptic sensations to the user so that, even though the indicia B1-B8 is flat and devoid of tactilely significant surfaces, the user is given the impression that a physical button actually exists, such as a push-button. Thus, each separate indicia B1-B8 may be coincident with and indicative of the location of a separate virtual button. Vibration generation system 120 may also cause sounds to be generated (i.e., auditory pressure waves) when the user positions a finger or the like on or proximate one or more indicia B1-B8. For example, a confirmation sound or another form of auditory feedback may be generated by vibration generation system 120 when the user positions a finger on or over an indicia B1-B8 to enable the user to confirm that the indicia B1-B8 has been selected by the user. For any given indicia B1-B8, auditory and haptic feedback may be provided by a common vibrational exciter 122 or by separate vibrational exciters 122 of the vibration generation system 120.

The indicia B1 and B2 are associated with raising (B1) or lowering (B2) an angle of the fowler section of the patient support deck 38. The indicia B3 and B4 are associated with lifting (B1) or lowering (B2) the patient support surface 42 relative to the floor surface, respectively. The indicia B5 and B6 are associated with lengthening (B5) or shortening (B6) the bed length extension device 80 to lengthen or shorten the patient support apparatus 30 to accommodate taller or shorter patients. The indicia B7 and B8 are associated with widening (B7) or narrowing (B8) the bed width extension device 82 to widen or narrow the patient support apparatus 30 to accommodate larger or smaller patients, respectively. Other indicia, not shown, is also contemplated for use with other functions of the patient support apparatus 30.

Figure 7:
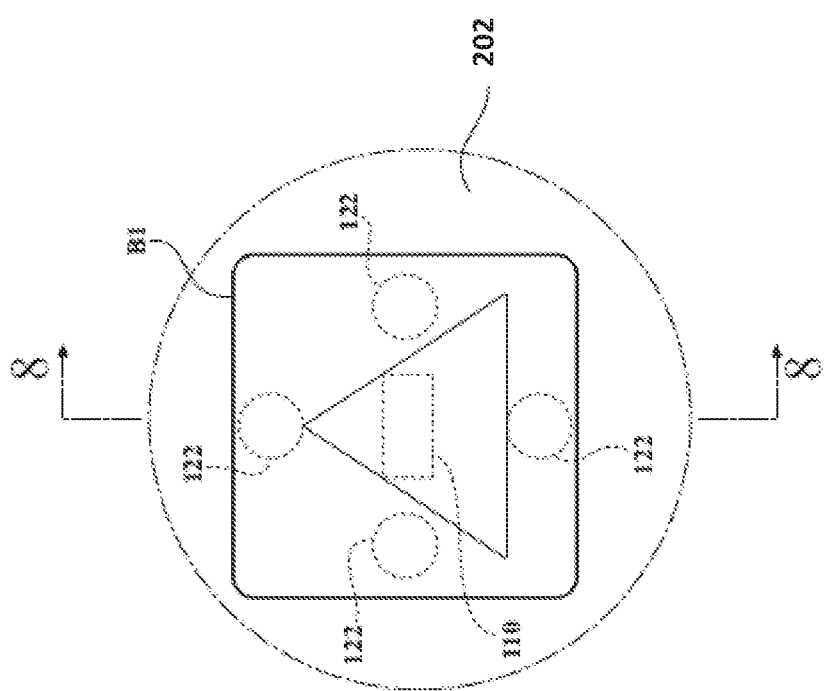
FIG. 7 is a blown-up view taken from FIG. 5 of indicia on the side rail.

Referring to FIG. 7, a close-up view of the indicia B1 is shown to illustrate the user input device 110 and vibrational exciters 122 that can be associated with the indicia B1 (and, in a similar manner, with the indicia B2-B8). As shown, a user input device 110 is associated with the indicia B1 to transmit signals to the controller 102 associated with the function attributed to the indicia B1. While a single user input device 110 is illustrated in FIG. 7 as being associated with the indicia B1, it should be recognized that the user input devices 110 of the various indicia B1-B8 may be separate, integrated into a single unit, or combinations thereof. The separate indicia B1-B8 provide the user with a visual indication of the location of the user input device or devices 110. For example, in one embodiment, a single user input device 110 may be associated with two or more of the indicia B1-B8 such that the two or more indicia may indicate the location of the user input device 110. It should be recognized that any suitable number of user input devices 110 may be included that are each associated with any number of indicia.

In the embodiment shown in FIGS. 8A and 8B, the separate indicia B1-B8 are located over their respective user input devices 110. In the embodiment shown, the separate user input devices 110 are located behind a respective panel 202, beneath each of the separate indicia B1-B8 and thus, are not visible to the user. The user input devices 110 may also be embedded in a respective panel 202.

In one embodiment, the user input devices 110 are capable of sensing user input and providing associated input signals to the controller 102 without requiring direct contact by the user. This further simplifies the exterior surface 137 of the barrier wall 132, allowing the use of a continuous, seamless barrier wall 132 in some cases, further easing cleaning and sanitizing of the barrier wall 132. The user input devices 110 may be mounted to panels 202 incorporated within the barrier wall 132 to detect user input through the panels 202 in the first region 134. Alternatively, the user input devices 110 may be incorporated within a pendant wearable around a neck of the user or another device wearable by the user.

In other embodiments, one or more user input devices 110, such as one or more piezoelectric sensors, may be used in conjunction with two, three, or more of the indicia B1-B8. For example, four piezoelectric sensors could be located about the control panel CP2, with the controller 102 being able determine a location at which the user is applying pressure (e.g., which indicia B1-B8 is being contacted) based on relative signals from the various piezoelectric sensors. A single piezoelectric sensor could similarly be used for multiple indicia by utilizing signal strength as an indication of location.

In one embodiment, one or more vibrational exciters 122 are associated with each of the separate indicia B1-B8 to provide haptic feedback to the indicia B1-B8. For example, as the user's finger contacts a user input device 110 associated with one of the indicia B1-B8, the user input device 110 transmits a signal to the controller 102. In response, the controller 102 may transmit an excitation signal to the vibrational exciter 122 to cause the vibrational exciter 122 to provide haptic feedback to the user as the user's finger is in contact with the indicia B1-B8 and/or the user input device 110.

In another embodiment, one or more vibrational exciters 122 are associated with each of the separate indicia B1-B8 to give the user the impression of a physical, raised surface (e.g., virtual button) protruding from the panel 202 at each of the separate indicia B1-B8. For example, referring to FIG. 8A, the user's finger is shown receiving haptic sensations produced by the vibrational exciters 122 when the user's finger is in close proximity to exciters 122. The haptic sensations may give the user the tactile sensation similar to an actual raised surface, but without requiring contact with the panel 202. As the user moves their finger through the pressure waves toward the panel 202, the user continues to receive the tactile sensation until the indicia B1 on the exterior surface of the panel 202 is reached. Once the user makes contact with the exterior surface and applies a force to the panel 202, the user input device 110 senses the force. In some cases, this can be through deflection of the panel 202, as shown in FIG. 8B (deflection exaggerated for illustration). Due to the connection between the user input device 110 and the controller 102, the controller 102 responds to sensing the user's applied force by performing the function desired by the user.

The user input devices 110 associated with the indicia B1 and B2, for instance, upon actuation, cause the controller 102 to energize the deck adjustment device 84 to articulate the fowler section of the patient support deck 38. The user input devices 110 associated with the indicia B3 and B4, upon actuation, cause the controller 102 to energize the lift device 78 to lift or lower the patient support surface 42 relative to the floor surface, respectively. The user input devices 110 associated with the indicia B5 and B6, upon actuation, cause the controller 102 to energize the bed length extension device 80 to lengthen or shorten the patient support apparatus 30 to accommodate taller or shorter patients. The user input devices 110 associated with the indicia B7 and B8, upon actuation, cause the controller 102 to energize the bed width extension device 82 to widen or narrow the patient support apparatus 30 to accommodate larger or smaller patients, respectively. Other user input devices, not shown, are contemplated for use with other indicia to perform other functions.

Still referring to FIGS. 8A and 8B, the barrier wall 132 defines an interior 135 generally isolated from the user between two barrier walls 132. It should be appreciated that, in some cases, the interior 135 is not completely inaccessible to the user or others, and may be accessed for service, cleaning, etc. On the other hand, the exterior surface 137 is exposed to the user and easily accessible to the user. While two barrier walls 132 are illustrated, it should be appreciated that a single barrier wall 132 may be provided such that the user input devices 110 are integrated into, or coupled to, the barrier wall 132. In the embodiment shown, the user input devices 110 are coupled to respective panels 202 integrated or embedded within the barrier wall 132. Alternatively, the user input devices 110 and/or vibrational exciters 122 may be embedded in the barrier wall 132, or may be coupled to the interior surface of the barrier wall 132. The user input devices 110 are thus disposed in the interior 135 such that the barrier walls 132 and panels 202 separate the user input devices 110 from the user in the first region 134. Additionally, the vibrational exciters 122 are disposed in the interior 135 such that the barrier walls 132 and panels 202 also separate the vibrational exciters 122 from the user in the first region 134. The user input devices 110 and/or vibrational exciters 122 may be present in one or more separate layers attached to the panels 202 or may be mounted to the panels 202 or barrier wall 132 in other ways. In some embodiments, the interior 135 may be defined by a single barrier wall 132. In this case, the user may be able to easily access the interior and the associated user input devices 110 and/or vibrational exciters 122 located therein even though the barrier wall 132 separates them from the user in the first region 134. In some embodiments, the barrier wall 132 may be multi-layered such that the barrier wall 132 is formed of multiple layers of the same or different materials. Thus, in some embodiments, the user input devices 110, vibrational exciters 122, and/or panels 202 may be coupled to or embedded within one or more of the multiple layers of the barrier wall 132. Alternatively, the barrier wall 132 may be formed of a single layer of material. In embodiments in which the user input devices 110 and/or vibrational exciters 122 are positioned behind a single barrier wall 132 or in an interior 135 of two barrier walls 132, the user input devices 110 and/or vibrational exciters 122 may be coupled directly to the interior surface of the barrier wall 132 or may be spaced apart from the barrier wall 132 by a bracket, a layer of intermediate material, or another suitable arrangement. In other embodiments, user input devices 110, panels 202, and/or vibrational exciters 122 may be positioned within one or more openings formed within barrier wall 132 (e.g., within one or more openings formed in exterior surface 137), may be positioned behind an access door or folding panel of the barrier wall 132, behind or within a portion of the barrier wall 132, may be embedded within a portion of barrier wall 132, and/or may be positioned in any other suitable location with respect to exterior surface 137 and/or barrier wall 132 that enables a patient or caregiver to access the user input devices 110, vibrational exciters 122, and/or panels 202.

The first region 134 defines a user interaction zone of the user interface that comprises the control panel CP2. In some embodiments, owing to the panel 202 being a smooth, generally flat surface in the first region 134, without any penetrations, seams/joints, etc., sanitizing of the user interaction zone is made easier and generally more effective than conventional user interaction zones that comprise undulating surfaces with penetrations, seams, and/or joints.

The panels 202 may be configured to transmit pressure waves. For instance, as described more fully herein, the panels 202 may have suitable dimensions (e.g., thickness) that enable pressure wave transmission, may be formed of materials that facilitate propagation of desired pressure wave frequencies, and the like. The controller 102 is coupled to the user input devices 110 and the vibrational exciters 122 and is configured to control the vibrational exciters 122 to produce pressure waves with the panel 202 in the first region 134 to provide haptic sensations and/or auditory outputs to the user. The controller 102 may also be located in the interior 135, or may be in communication with the user input devices 110 and the vibrational exciters 122 through one of the barrier walls 132. In the embodiment shown in FIG. 3, the first region 134 may include a portion of an electronic display, such as a portion of the control panel CP. In the embodiment shown in FIG. 5, the panels 202 are free of any electronic visual displays in at least the first region 134, i.e., the user interaction zone. In other embodiments, one of the panels 202 may be free of such electronic visual displays in the first region 134, while one or more electronic visual displays are located outside the first region 134, on another panel 202, or elsewhere.

In some cases, the tactile sensations and/or audio outputs may be different for each of the separate functions using the methods described above. In other words, the audio outputs and/or haptic sensations associated with each of the separate indicia B1-B8 may be different. As a result, the user is able to operate certain functions on the patient support apparatus 30 solely by feel and/or sound if needed, thereby freeing the user's attention to focus on the patient or on other tasks. The controller 102 is also capable of virtually increasing or decreasing the size of the virtual button and/or increasing or decreasing the intensity of auditory output generated to accommodate different users or for different functions. For example, the controller 102 may increase or decrease the size of the virtual button by increasing or decreasing the amplitude of the audio and/or haptic outputs to provide the sensation that the virtual button is a larger or smaller size in some embodiments.

Figure 9:
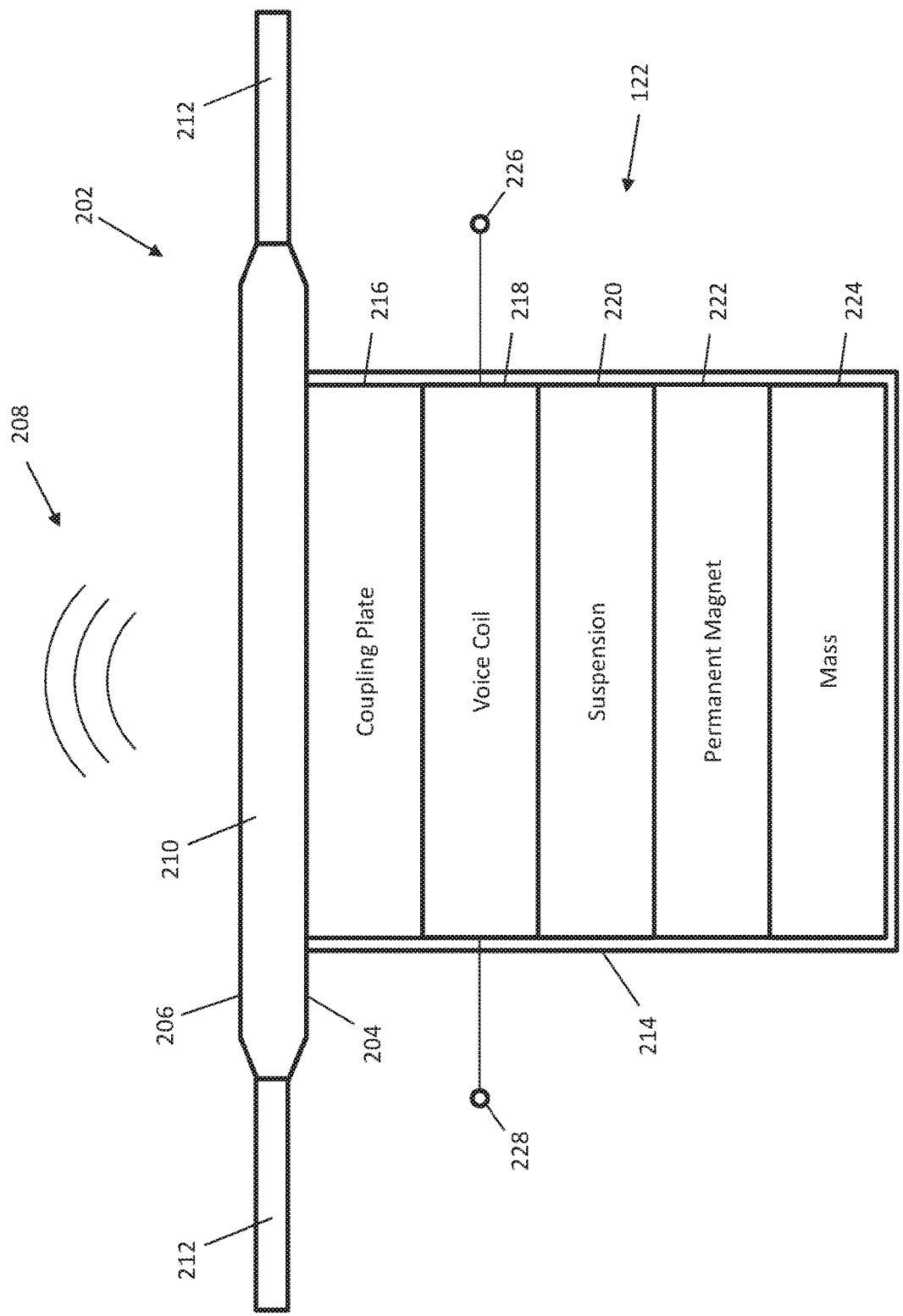
FIG. 9 is a block diagram of a vibrational exciter.

FIG. 9 is a block diagram of one example of the vibrational exciter 122 that may be used with patient support apparatus 30 (shown in FIG. 1). The vibrational exciter 122 may be directly coupled to a panel 202 of the patient support apparatus 30 to cause the panel 202 to vibrate and propagate pressure waves (e.g., auditory or haptic pressure waves) as described more fully herein.

The panel 202 and the vibrational exciter 122 may be included within the barrier wall 132 or another portion of a side rail 44, 46, 48, or 50, headboard 52, footboard 54, caregiver interface 56, and/or any other suitable portion of the patient support apparatus 30. In one embodiment, the panel 202 and the vibrational exciter 122 may be included within a movable portion of the patient support deck 38, such as a fowler section or a foot section of the patient support deck 38. The panel 202 comprises an interior surface 204 and a planar, arcuate, or other suitably shaped exterior surface 206. The vibrational exciter 122 may be directly coupled to the interior surface 204 of the panel 202 such that the vibrational exciter 122 is concealed behind the exterior surface 206, thus improving the aesthetics of the panel 202 and the vibrational exciter 122. In one embodiment, the exterior surface 206 is solid and impermeable. The exterior surface 206 may face the patient when the patient is supported by the patient support apparatus 30. In a specific embodiment, the exterior surface 206 of the panel 202 forms a part of the exterior surface 137 of a barrier wall 132 facing the patient. For example, in an embodiment in which the panel 202 and the vibrational exciter 122 are included within a portion of the side rail 44, the exterior surface 206 of the panel 202 may be a portion of the surface of the side rail 44 facing the patient. Alternatively, the exterior surface 206 of the panel 202 may be positioned within another suitable portion of the patient support apparatus 30 such that the exterior surface 206 faces away from the patient, or in any other suitable direction with respect to the patient or the patient support apparatus 30.

In a specific embodiment, the vibrational exciter 122 is sealed within the portion of the patient support apparatus 30 (e.g., within the interior 135 of the barrier wall 132). As a result of the solid and impermeable exterior surface 206 of the panel 202 and the fact that the vibrational exciter 122 may be sealed within the portion of the patient support apparatus 30, biomaterial may be prevented from entering the panel 202 and the vibrational exciter 122 from the patient or from other sources. This arrangement of the panel 202 and the vibrational exciter 122 provides an easily cleanable exterior surface 206 as compared with surfaces having speaker grills with holes. In addition, the substantially sealed construction of the vibrational exciter 122 reduces an unintended introduction of fluids into the vibrational exciter 122, thus minimizing electrical failures of the vibrational exciter 122 as compared to conventional speakers that might otherwise be used with the patient support apparatus 30. The vibrational exciter 122 may also be enabled to fit into portions of the patient support apparatus 30 that conventional speakers may be prevented from being placed due to size constraints associated with conventional speaker diaphragms, for example.

The panel 202 may be physically adapted to vibrate at one or more frequencies. In one embodiment, the panel 202 may be physically adapted to vibrate at audible frequencies within the range of 20 hertz (Hz) to 20 kilohertz (kHz). Additionally or alternatively, the panel 202 may be physically adapted to vibrate at haptic frequencies within the range of 0.2 Hz to 500 Hz or above 20 kHz (i.e., ultrasonic frequencies). To enable the panel 202 to vibrate at one or more desired frequencies, the panel 202 may be formed of one or more materials such as aluminum, plastic, resin, fiberglass, glass, and/or another suitable material. For example, dense materials may enable the panel 202 to vibrate and output pressure waves 208 at higher frequencies as compared to less dense materials, while more flexible materials may enable the panel 202 to vibrate and output pressure waves 208 at lower frequencies as compared to less flexible materials. In addition, a thickness of the panel 202 may affect the ability of the panel 202 to vibrate at the desired frequencies. For example, a relatively thick panel 202 may cause the panel 202 to output pressure waves 208 at lower frequencies than a relatively thin panel 202.

In addition, the panel 202 may comprise two or more sections having different properties. For example, as shown in FIG. 9, the panel 202 may comprise a vibrating section 210 and one or more adjacent sections 212 that have different thicknesses, densities, rigidity characteristics (e.g., having internal or external ribbing, brackets, cavities, etc.) and/or that are formed of different materials. In some embodiments, the vibrating section 210 and adjacent sections 212 may have the same coatings applied to their respective surfaces, or alternatively may have a different coating applied. The coatings may include anti-microbial coatings and/or any other suitable coating. In one embodiment, the vibrational exciter 122 is coupled to the vibrating section 210 to cause vibrations from the vibrational exciter 122 to be transferred to the vibrating section 210. In one embodiment, the vibrating section 210 may have a different thickness than a thickness of adjacent sections 212, such as being thicker (as illustrated in FIG. 9) or thinner than the adjacent sections 212. As described above, the selection of the different properties of the vibrating section 210 and/or adjacent sections 212 enable the vibrating section 210 (and thus the panel 202) to output pressure waves at the desired frequencies. Furthermore, between the vibrating section 210 and the adjacent sections 212 may be thinning of material to define a general area of the vibrating section 210 and to enable the vibrating section 210 to move relative to the adjacent sections 212.

In one embodiment, as shown in FIG. 9, the vibrational exciter 122 comprises a plurality of components disposed within a housing 214. While the housing 214 is illustrated in FIG. 9 as being one integral structure, it should be recognized that the housing 214 may comprise any suitable number of portions that may be fixed or movable with respect to each other. The components of the vibrational exciter 122 may comprise, for example, a coupling plate 216, a voice coil 218, a suspension 220, a permanent magnet 222, and an optional mass 224.

In one embodiment, the coupling plate 216 is a metal plate or other surface that enables the vibrational exciter 122 to be securely and directly coupled to the panel 202. For example, the coupling plate 216 may be coupled to the interior surface 204 of the panel 202 using a suitable adhesive. Alternatively, the coupling plate 216 may be indirectly coupled to the interior surface 204 of the panel 202 through an intermediate panel, bracket, or other mechanism or material. In other embodiments, the coupling plate 216 may be formed of plastic or another suitable material, and/or may be coupled to the interior surface 204 using another suitable coupling mechanism other than adhesive, such as one or more screws, bolts, etc. Alternatively, the coupling plate 216 may be omitted in some embodiments such that the voice coil 218 is coupled directly or indirectly to the interior surface 204 of the panel 202.

The voice coil 218 is a conductive coil that receives an electrical signal (hereinafter referred to as an "excitation signal") from the controller 102 or another suitable signal source via terminals 226 and 228. The excitation signal is a sinusoidal signal or another suitable signal that alternates polarity under the control of the controller 102. In one embodiment, the voice coil 218 is coupled to the coupling plate 216. Alternatively, the voice coil 218 may be coupled to a suitable portion of the housing 214. The transmission of the excitation signal through the voice coil 218 causes a magnetic field to be generated. The polarity of the magnetic field is based on the polarity of the excitation signal transmitted through the voice coil 218 such that the polarity of the magnetic field switches when the polarity of the signal changes.

The suspension 220 is coupled to a portion of the housing 214 between the voice coil 218 and the permanent magnet 222. In one embodiment, the suspension 220 comprises a plurality of springs or other elastic members that enable the voice coil 218 and the permanent magnet 222 to move in relation to each other. In addition, the suspension 220 facilitates maintaining the voice coil 218 in a spaced and centered relationship with the permanent magnet 222.

The permanent magnet 222 generates a magnetic field having a fixed polarity. In one embodiment, the magnetic field generated by the permanent magnet 222 interacts with the magnetic field generated by the voice coil 218 to either attract or repel the permanent magnet 222 and the voice coil 218. By alternating the polarity of the magnetic field generated by the voice coil 218, vibrations are produced within the vibrational exciter 122 due to the alternating attraction and repelling of the fields. In some embodiments, the positions of the voice coil 218 and the permanent magnet 222 within the housing 214 may be switched.

A mass 224 may be included in the vibrational exciter 122 in some embodiments. If included, the mass 224 increases the mass of the vibrational exciter 122 which in turn increases the amplitude of the vibrations generated by the vibrational exciter 122.

During operation, the excitation signal is transmitted from the controller 102 or another suitable source through the voice coil 218 via the terminals 226 and 228. The controller 102 alternates the polarity of the excitation signal at one or more selected frequencies to cause the voice coil 218 to generate a magnetic field with a polarity that alternates at the excitation signal frequencies. The alternating magnetic field interacts with the magnetic field generated by the permanent magnet 222 to generate forces that alternatingly attract and repel the voice coil 218 and the permanent magnet 222.

The suspension 220 is at least partially elastic to enable the alternating attracting and repelling forces to cause the permanent magnet 222 and the voice coil 218 to move toward and away from each other. This alternating movement causes vibrations to be induced within the vibrational exciter 122. Specifically, the vibrations are propagated through the vibrational exciter 122, through the coupling plate 216, and into the panel 202 due to the direct coupling of the vibrational exciter 122 to the panel 202. The vibrations have one or more frequencies that substantially match the frequencies of the excitation signal provided by the controller 102. The vibrations propagate through the panel 202 as pressure waves that are then transferred to the ambient air as auditory (sound) pressure waves and/or to a portion of a user's anatomy (e.g., a user's finger) in contact with, or in close proximity to, the panel 202 as haptic pressure waves. Thus, the vibrational exciter 122 converts the excitation signal to vibrational energy that is transferred to the exterior surface 206 of the panel 202 to cause the panel 202 to vibrate at the auditory and/or haptic frequencies.

Figure 10:
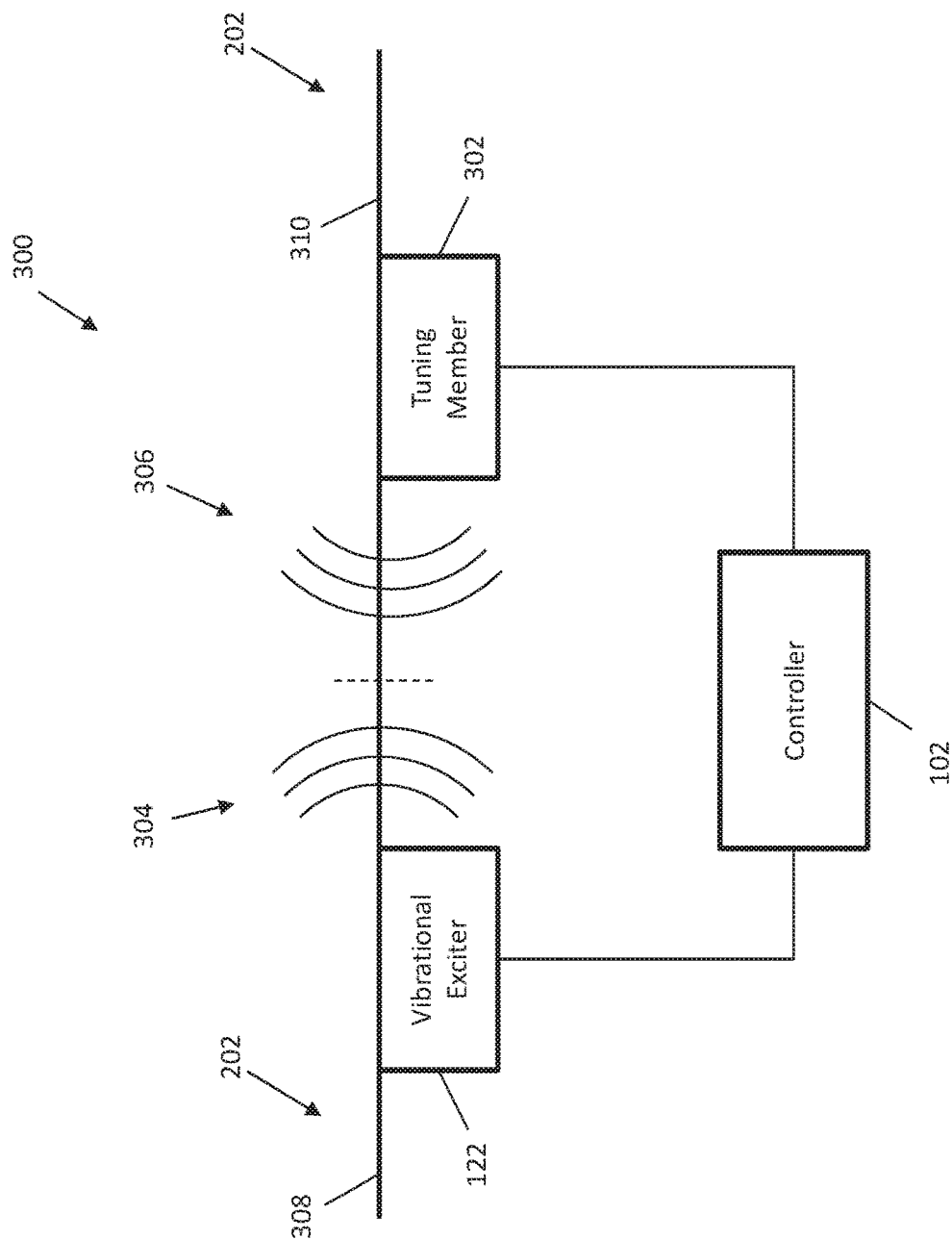
FIG. 10 is a block diagram of a vibrational system.

FIG. 10 is a block diagram of a vibrational system 300, according to one example, that may be used with the patient support apparatus 30 (shown in FIG. 1). In the embodiment illustrated in FIG. 10, the system 300 comprises a vibrational exciter 122 and a tuning member 302 that are coupled to the controller 102. While one vibrational exciter 122, one tuning member 302, and one controller 102 are illustrated in FIG. 10, it should be recognized that any suitable number of vibrational exciters, tuning members, and/or controllers may be used as desired.

In the embodiment illustrated in FIG. 10, the vibrational exciter 122 and the tuning member 302 are arranged on one or more panels 202 to interact with each other. More specifically, the vibrational exciter 122 and the tuning member 302 are arranged such that the pressure waves 304 generated by the vibrational exciter 122 may interact with the pressure waves 306 generated by the tuning member 302. While the pressure waves 304 and 306 are illustrated in FIG. 10 as propagating toward each other only in a planar direction, this is shown solely for clarity of illustration. It should be recognized that the pressure waves 304 and 306 may propagate in a variety of directions, including in a hemispherical direction emanating outward from each vibrational exciter 122 or tuning member 302. In one embodiment, the vibrational exciter 122 is directly coupled to the same panel 202 as the tuning member 302, such as being coupled to the vibrating section 210 of the same panel 202. Alternatively, the vibrational exciter 122 may be coupled to a first panel 308 while the tuning member 302 may be coupled to a second panel 310 that is in turn coupled directly or indirectly to the first panel 308 such that vibrations from the second panel 310 are transferred to the first panel 308 and vice versa. In other words, the vibration of the second panel 310 may cause the first panel 308 to vibrate, and vice versa.

In one embodiment, the vibrational exciter 122 is a first vibrational exciter and the tuning member 302 is a second vibrational exciter. Alternatively, the tuning member 302 may be a piezoelectric sensor, an eccentric rotating mass vibration motor, and/or any other suitable device that may generate pressure waves at one or more selected frequencies.

The controller 102 may control the tuning member 302 to generate pressure waves 306 that interact with the pressure waves 304 of the vibrational exciter 122. In a specific embodiment, the controller 102 causes the tuning member 302 to generate pressure waves 306 that reduce the amplitude of the pressure waves 304 generated by the vibrational exciter 122, such by causing the tuning member pressure waves 306 to have one or more frequencies that are shifted 180 degrees from the frequencies of the vibrational exciter pressure waves 304. In such an embodiment, the tuning member 302 dampens the vibrational exciter pressure waves 304. This may be useful in situations where the controller 102 desires to mute or otherwise reduce a volume of sound or intensity of haptic feedback generated from the vibrational exciter 122. In another embodiment, the controller 102 causes the tuning member 302 to generate pressure waves 306 that increase the amplitude of the pressure waves 304 generated by the vibrational exciter 122, such by causing the tuning member pressure waves 306 to have one or more frequencies that are the same as the frequencies of the vibrational exciter pressure waves 304. In such an embodiment, the tuning member 302 enhances or increases the vibrational exciter pressure waves 304. This may be useful in situations where the controller 102 desires to increase a volume of sound or haptic feedback generated from the vibrational exciter 122.

In addition, the controller 102 may operate one vibrational exciter 122 to measure or assess the performance of another vibrational exciter 122 and associated panel 202. For example, a first vibrational exciter 122 and an associated first panel 202 may receive pressure waves from a second vibrational exciter 122 and an associated second panel 202. The pressure waves received by the first vibrational exciter 122 may cause the voice coil 218 and the permanent magnet 222 of the first vibrational exciter 122 to move in relation to each other, thus creating a fluctuating magnetic field that induces a current through the voice coil 218. The current may be received by the controller 102 as a signal (hereinafter referred to as a "vibration response signal"). The controller 102 may analyze the vibration response signal to determine the intensity of the vibrations received from the second vibrational exciter 122 and the second panel 202. The controller 102 may thus assess the performance of the second vibrational exciter 122 and the second panel 202, and may transmit a signal to a remote computing device to notify the remote computing device accordingly. Additionally or alternatively, the controller 102 may alter the operation of the first vibrational exciter 122, the second vibrational exciter 122, and/or one or more other vibrational exciters 122 to increase or decrease the vibrations generated by the second vibrational exciter 122, for example.

Figure 11:
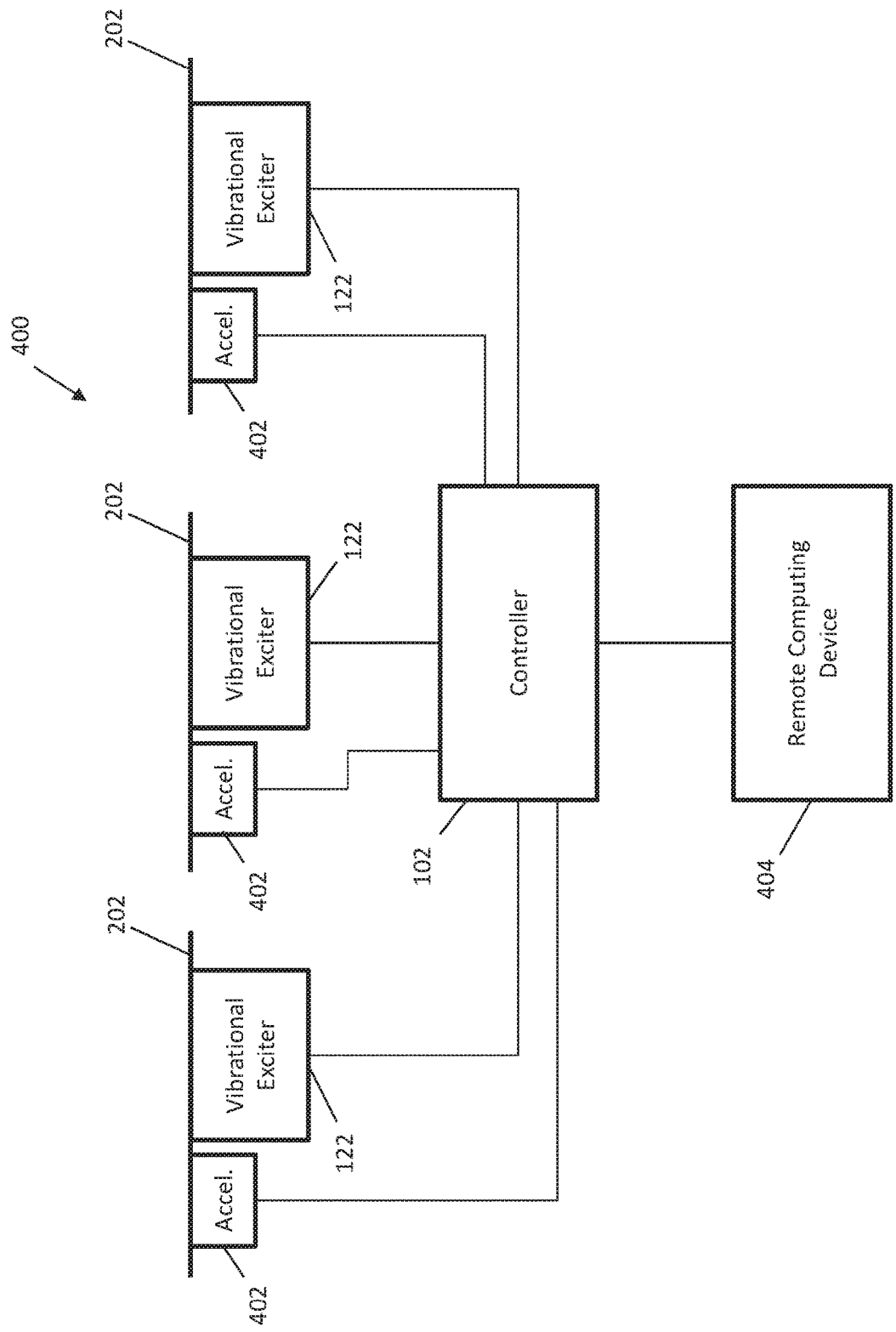
FIG. 11 is a block diagram of another vibrational system.

FIG. 11 is a block diagram of another vibrational system 400 that may be used with the patient support apparatus 30 (shown in FIG. 1). In this embodiment, one or more vibrational exciters 122 are coupled to respective panels 202 (or to the same panel 202). In addition, one or more accelerometers 402 are coupled to respective panels 202 (or the same panel 202) to generate measurements related to vibrations induced within each panel 202. In the specific embodiment shown in FIG. 11, an accelerometer 402 may be coupled to a panel 202 proximate each vibrational exciter 122 to measure vibrations induced by each vibrational exciter 122. While FIG. 11 illustrates a single controller 102 coupled to each accelerometer 402 and vibrational exciter 122, it should be recognized that a separate controller 102 may be coupled to each accelerometer 402 and/or vibrational exciter 122, or any suitable number of controllers 102 may be used as desired. While the controller 102 is illustrated in FIG. 11 as being coupled to a remote computing device 404, it should be recognized that the controller 102 may be coupled to any other suitable device within the patient support apparatus 30 and may transmit signals and data described herein to the devices within the patient support apparatus 30 in addition to the remote computing device 404.

In one embodiment, the accelerometers 402 are piezoelectric sensors that generate an electrical signal (referred to herein as a "vibration signal") having an amplitude and frequency based on the movement of the panel 202 resulting from the panel's vibration. Alternatively, the accelerometers 402 may be micro-electrical mechanical system (MEMS) sensors or any other suitable sensor that measures vibration or movement. The vibration signal is transmitted to the controller 102 for analysis and/or storage within a memory.

The controller 102 receives the vibration signal and analyzes the signal to determine or verify an operation of the vibrational exciter 122 and/or the panel 202. In one embodiment, the controller 102 compares an amplitude and/or a frequency of the vibration signal to a predetermined amplitude and/or frequency threshold to determine whether the vibrational exciter 122 is operating properly. For example, the controller 102 may determine that the vibrational exciter 122 is operating properly if the amplitude and/or frequency of the vibration signal is equal to or greater than the predetermined amplitude and/or frequency threshold. The controller 102 may determine that the vibrational exciter 122 is not operating properly if the amplitude and/or frequency of the vibration signal is less than the predetermined amplitude and/or frequency threshold.

Alternatively, the controller 102 may compare the amplitude and/or frequency of the vibration signal to the amplitude and/or frequency of the excitation signal transmitted from the controller 102 to determine whether the vibrational exciter 122 is operating properly. In the alternative embodiment, the controller 102 may determine that the vibrational exciter 122 is operating properly if the amplitude and/or frequency of the vibration signal is a predetermined percentage of the amplitude and/or frequency of the excitation signal. The controller 102 may determine that the vibrational exciter 122 is not operating properly if the amplitude and/or frequency of the vibration signal is less than the predetermined percentage of the amplitude and/or frequency of the excitation signal. In another embodiment, the controller 102 may determine whether the vibrational exciter 122 is operating properly by comparing the vibration signal to expected vibration values based on the excitation signal transmitted to the vibrational exciter 122 in conjunction with calibration data about the vibrational exciter 122 and its associated panel 202. For example, each vibrational exciter 122 and panel 202 may vibrate at slightly different frequencies and/or amplitudes such that each vibrational exciter 122 and panel 202 may need to be calibrated to vibrate at a consistent frequencies and amplitude with respect to each other vibrational exciter 122 and/or panel 202. Each vibrational exciter 122 and/or panel 202 may therefore have calibration data stored in a memory readable by the controller 102 to enable the controller 102 to adjust the excitation signal transmitted to each vibrational exciter 122 to cause each vibrational exciter 122 and/or panel 202 to vibrate at a desired frequency and amplitude. Therefore, in determining whether each vibrational exciter 122 is operating properly, the controller 102 may compare the vibration signal to expected values associated with the vibration signal based on the excitation signal provided to the vibrational exciter 122 and the calibration data associated with the vibrational exciter 122.

If the controller 102 determines that the vibrational exciter 122 is operating properly, the controller 102 may transmit a verification message to a remote computing device 404 and/or to another suitable device within the patient support apparatus 30 to indicate proper operation of the exciter 122. If the controller 102 determines that the vibrational exciter 122 is not operating properly, the controller 102 may transmit an error message to the remote computing device 404 to indicate that the exciter 122 did not produce an expected vibration signal (and thus, did not produce an expected amount of vibration within the panel 202). Additionally or alternatively, if the controller 102 determines that the vibrational exciter 122 or its associated panel 202 is not operating properly, the controller 102 may automatically modify the excitation signal transmitted to the vibrational exciter 122 to cause the vibrational exciter 122 and its associated panel 202 to output the desired vibrational amplitude and/or frequency.

In one embodiment, an accelerometer 402 may also measure the vibrations or pressure waves generated by other vibrational exciters 122 within the patient support apparatus 30 in addition to generating its own vibrations or pressure waves. For example, an accelerometer 402 positioned within a side rail (e.g., the side rail 46) may measure the pressure waves generated by a vibrational exciter 122 that is positioned in an opposing side rail (e.g., the side rail 50) as the pressure waves are received by and propagated through the side rail 46 to the accelerometer 402. The controller 102 may thereby verify or assess the operation of the panels 202 other than the panel 202 to which the accelerometer 402 is coupled. For example, an accelerometer 402 may be coupled to a panel 202 that is not currently operating (i.e., not currently vibrating), and the controller 102 may use the non-operating panel 202 (with the attached accelerometer 402) to assess or verify the operation of another panel 202.

In another embodiment, the same accelerometer 402 that outputs and/or measures auditory and/or haptic pressure waves described herein may also detect and/or measure a movement of the patient support apparatus 30, or a portion thereof, and may transmit a signal representing the detected movement to the controller 102. For example, the accelerometer 402 may detect a patient or caregiver raising or lowering a portion of the patient support apparatus 30, such as a side rail 44, 46, 48, 50, and may transmit a signal representing the detected movement of the side rail. The accelerometer 402 may detect and/or measure the movement of a portion of the patient support apparatus 30 that the accelerometer 402 is coupled to, and may also detect and/or measure the movement of another portion of the patient support apparatus 30 that the accelerometer 402 is not directly coupled to. For example, in one embodiment, an accelerometer 402 may be coupled to a headboard 52 of the patient support apparatus 30. If the patient or caregiver moves a footboard 54 of the patient support apparatus 30, resulting vibrations associated with the movement may propagate through the intermediate frame 36 and/or patient support deck 38, for example, to the headboard 52 and may be detected and/or measured by the accelerometer 402. Other related movements associated with the patient support apparatus 30 may also be monitored, such as movements related to user inputs received through the control panel CP or CP 2. By monitoring the signals transmitted by the accelerometer 402, the controller 102 may verify operation of various portions of the control panel CP or CP2 that are intended to cause movement of respective portions of the patient support apparatus 30 when selected by a user.

In one embodiment, the remote computing device 404 is coupled to the controller 102 to receive the verification messages and error messages identified above. The remote computing device 404 may comprise, for example, a computer, a smart phone, a PDA, a laptop, a tablet computing device, a nurse call station, a server, and/or any other suitable device coupled to the controller 102. The remote computing device 404 may also transmit signals to the controller 102 including audio or haptic source signals to enable the controller 102 to transmit the signals to the vibrational exciter 122. The audio source signals may comprise data representative of spoken communications from a nurse or other caregiver (e.g., a nurse callback), music data from one or more music files or video files, data representative of user interface commands or auditory feedback, and the like that may be audibly transmitted to a patient or other recipient through the controller 102 and the vibrational exciter 122. Haptic source signals may comprise data representative of a number, amplitude, and/or frequency of haptic feedback that may be haptically transmitted to the patient or other recipient through the controller 102 and the vibrational exciter 122.

In one embodiment, one or more vibrational exciters 122 may be used to impart or simulate massage therapy to a patient who is being supported by the patient support apparatus 30. The vibrational exciters 122 may be integrated within, or coupled to, the patient support deck 38, the mattress 40, the patient support surface 42, and/or another suitable portion of the patient support apparatus 30. The controller 102 may transmit excitation signals to the vibrational exciters 122 to cause the vibrational exciters 122 to propagate haptic pressure waves to the patient through the portion of the patient support apparatus 30. The controller 102 may thus control the panel or panels 202 coupled to the vibrational exciters 122 to vibrate at one or more frequencies adapted to stimulate various sensory receptors of the patient to provide massage therapy to the patient. In another embodiment, pods or other containers may be filled with air or other fluids underneath the patient. The vibrational exciters 122 may be coupled to the pods to propagate pressure waves through the pods and into the patient to provide massage therapy to the patient. The controller 102 may adjust the amplitude and frequency of the pressure waves used for the massage therapy based on user input (e.g., through the control panel CP or CP2), based on caregiver input, and/or based on a profile stored in a memory accessible by controller 102.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support apparatus comprising:
   a base;
   a support structure coupled to the base and being configured to support a patient;
   a panel having a surface and being physically adapted to vibrate at one or more frequencies;
   a controller configured to generate an electrical signal;
   a vibrational exciter comprising a surface coupled to the surface of the panel and being configured to receive the electrical signal from the controller and to convert the electrical signal into vibrational energy, and wherein the surface of the vibrational exciter is configured to transfer the vibrational energy to the surface of the panel to vibrate the panel at the one or more frequencies; and an accelerometer coupled to the panel and to the controller, wherein the accelerometer is configured to produce measurements indicative of vibrations of the panel induced by the vibrational exciter, and wherein the controller is configured to analyze the measurements from the accelerometer to assess and confirm a proper operation of the vibrational exciter and/or the panel based on a comparison of the measurements with predetermined values expected by the controller that define the proper operation of the vibrational exciter.

2. The patient support apparatus of claim 1, wherein the panel is solid and impermeable.

3. The patient support apparatus of claim 1, further comprising a side rail coupled to the support structure and wherein the side rail comprises the panel and the vibrational exciter.

4. The patient support apparatus of claim 1, wherein the support structure comprises at least one of a headboard or a footboard, and wherein at least one of the headboard or the footboard comprises the panel and the vibrational exciter.

5. The patient support apparatus of claim 1, wherein the panel is physically adapted to vibrate at the one or more frequencies by further comprising a vibrating section and an adjacent section that is adjacent the vibrating section, and at least one of the following:

the vibrating and adjacent sections comprising different thicknesses;

the vibrating and adjacent sections comprising different densities;

the vibrating and adjacent sections comprising different materials; or the vibrating section comprising a tuning member integrally attached thereto and being configured to tune the vibrating section.

6. The patient support apparatus of claim 1, wherein the vibrational exciter is further configured to vibrate the panel at the one or more frequencies to provide a haptic and/or auditory response.

7. The patient support apparatus of claim 1, wherein the one or more frequencies are defined by a range between 20 hertz (Hz) and 20 kilohertz (kHz).

8. The patient support apparatus of claim 1, wherein the panel comprises an exterior surface and an interior surface, and wherein the surface of the vibrational exciter is coupled to the interior surface of the panel such that the vibrational exciter is concealed behind the exterior surface.

9. The patient support apparatus of claim 1, further comprising a user interface comprising the panel and the vibrational exciter and with the user interface being configured to enable user selection in response to tactile engagement of the panel.

10. The patient support apparatus of claim 9, wherein the vibrational exciter is configured to vibrate the panel of the user interface at the one or more frequencies to provide haptic and/or auditory feedback in response to tactile engagement of the panel.

11. The patient support apparatus of claim 1, wherein the panel is a first panel and wherein the patient support apparatus further comprises a second vibrational exciter configured to transfer vibrational energy to a surface of a second panel to vibrate the second panel, wherein the first panel is spaced apart from the second panel and the first panel is configured to vibrate in response to vibration of the second panel.

12. The patient support apparatus of claim 11, wherein the controller is configured to analyze the measurements from the accelerometer to assess operation of the second vibrational exciter and/or the second panel.

13. The patient support apparatus of claim 1, wherein the support structure comprises a surface being configured to support the patient, wherein the surface of the support structure comprises the panel and the vibrational exciter, and wherein the vibrational exciter is configured to vibrate the panel of the support structure at the one or more frequencies to provide massage therapy to the patient.

14. A method of providing audible and/or haptic output for a patient support apparatus, the patient support apparatus comprising a base, a support structure coupled to the base and being configured to support a patient, a panel having a surface and being physically adapted to vibrate at one or more frequencies, a controller, and a vibrational exciter comprising a surface coupled to the surface of the panel, the method comprising:

generating an electrical signal with the controller;

receiving, with the vibrational exciter, the electrical signal from the controller;

converting, with the vibrational exciter, the electrical signal to vibrational energy;

transferring, with the vibrational exciter, the vibrational energy to the surface of the panel for vibrating the panel at the one or more frequencies;

providing, with an accelerometer, measurements indicative of vibrations of the panel; and analyzing, with the controller, the measurements from the accelerometer for assessing and confirming a proper operation of the vibrational exciter and/or the panel by comparing the measurements with predetermined values expected by the controller that define the proper operation of the vibrational exciter.

15. The method of claim 14, wherein transferring the vibrational energy to the surface of the panel for vibrating the panel at the one or more frequencies causes the panel to provide a haptic and/or auditory response.

16. The method of claim 14, wherein the one or more frequencies are defined by a range between 20 Hz and 20 kHz.

17. The method of claim 14, wherein the patient support apparatus further comprises a user interface comprising the panel and the vibrational exciter, the method further comprising enabling, with the user interface, a user selection in response to tactile engagement of the panel.

18. The method of claim 17, further comprising vibrating the panel of the user interface at the one or more frequencies to provide audible and/or haptic feedback in response to tactile engagement of the panel.

19. The method of claim 14, wherein the panel is a first panel and the patient support apparatus further comprises a second vibrational exciter configured to transfer vibrational energy to a surface of a second panel that is spaced apart from the first panel, the method further comprising vibrating the second panel with the second vibrational exciter and vibrating the first panel in response to vibrating the second panel.

20. The method of claim 19, the method further comprising analyzing, with the controller, the measurements from the accelerometer for assessing operation of the second vibrational exciter and/or the second panel.

21. The method of claim 14, wherein the support structure comprises a surface for supporting the patient and wherein the surface of the support structure comprises the panel and the vibrational exciter, the method further comprising vibrating, with the vibrational exciter, the panel of the support structure at the one or more frequencies to provide massage therapy to the patient.

* * * * *